United States Patent [19]

Knippscheer et al.

[11] Patent Number: 5,233,844
[45] Date of Patent: Aug. 10, 1993

[54] STORAGE APPARATUS, PARTICULARLY WITH AUTOMATIC INSERTION AND RETRIEVAL

[75] Inventors: Hermann Knippscheer, Baldwin, N.Y.; Daniel D. Richard, Sedona, Ariz.; Stanley Rosenberg, Hewlett, N.Y.; Michael Murphy; John Vickery, both of Dublin, Ireland

[73] Assignee: Cryo-cell International, Inc., Baldwin, N.Y.

[21] Appl. No.: 745,636

[22] Filed: Aug. 15, 1991

[51] Int. Cl.⁵ ................................................ F25D 11/00
[52] U.S. Cl. ........................................ 62/440; 414/331
[58] Field of Search ................ 62/440, 381, 375; 414/331

[56] References Cited

U.S. PATENT DOCUMENTS

| | | |
|---|---|---|
| 1,938,985 | 12/1933 | Starr . |
| 2,928,705 | 3/1960 | Goldsmith . |
| 2,950,605 | 8/1960 | Hennion . |
| 3,034,845 | 5/1962 | Haumann . |
| 3,100,969 | 8/1963 | Elfving . |
| 3,141,123 | 7/1964 | Olson . |
| 3,227,501 | 1/1966 | Austin et al. . |
| 3,327,833 | 6/1967 | Jungner et al. . |
| 3,535,889 | 10/1970 | Curti ................................. 62/381 |
| 3,564,727 | 3/1969 | Fraser . |
| 3,583,171 | 6/1971 | Flynn . |
| 3,662,565 | 5/1972 | Gram ................................. 62/381 |
| 3,696,631 | 10/1972 | Valdes . |
| 4,124,992 | 11/1978 | Chmiel . |
| 4,199,022 | 4/1980 | Senkan et al. . |
| 4,245,483 | 1/1981 | Murai ................................. 62/376 |
| 4,304,293 | 12/1981 | Schweiwe . |
| 4,314,459 | 2/1982 | Rivoire . |
| 4,340,263 | 7/1982 | Webb . |
| 4,480,682 | 11/1984 | Kaneta et al. . |
| 4,531,373 | 7/1985 | Rubinsky . |
| 4,627,799 | 12/1986 | Terauchi . |
| 4,681,839 | 7/1987 | Swartz . |
| 4,712,607 | 12/1987 | Lindemans et al. . |
| 4,713,941 | 12/1987 | Toyoda et al. . |
| 4,722,058 | 1/1988 | Nakayama et al. . |
| 4,790,141 | 12/1988 | Glascock . |
| 4,870,829 | 10/1989 | Oullette et al. . |
| 5,125,240 | 1/1992 | Knippscheer et al. ............. 62/440 |

FOREIGN PATENT DOCUMENTS 2509762  9/1976  Fed. Rep. of Germany .

Primary Examiner—Ronald C. Capossela
Attorney, Agent, or Firm—R. Neil Sudol; Henry D. Coleman

[57] ABSTRACT

A storage unit comprises a housing defining a storage chamber and a plurality of specimen carriers in the form of annular shelves disposed one below the other inside the chamber. A rotary drive is operatively connected to the carriers for rotating the carriers independently about a vertical axis. The housing is provided with an access opening for enabling access to the chamber from above the carrier, while an insertion and removal mechanism serves to alternately insert and remove specimens from the chamber via the access opening. The insertion and removal mechanism includes a lifting device disposed at least partially inside the storage chamber for moving specimens vertically between the access opening and the respective carriers. Specimen-containing vials are disposed on trays which in turn are supported by the carriers. The lifting mechanism operates to lift entire trays from the respective carriers towards the access opening.

51 Claims, 9 Drawing Sheets

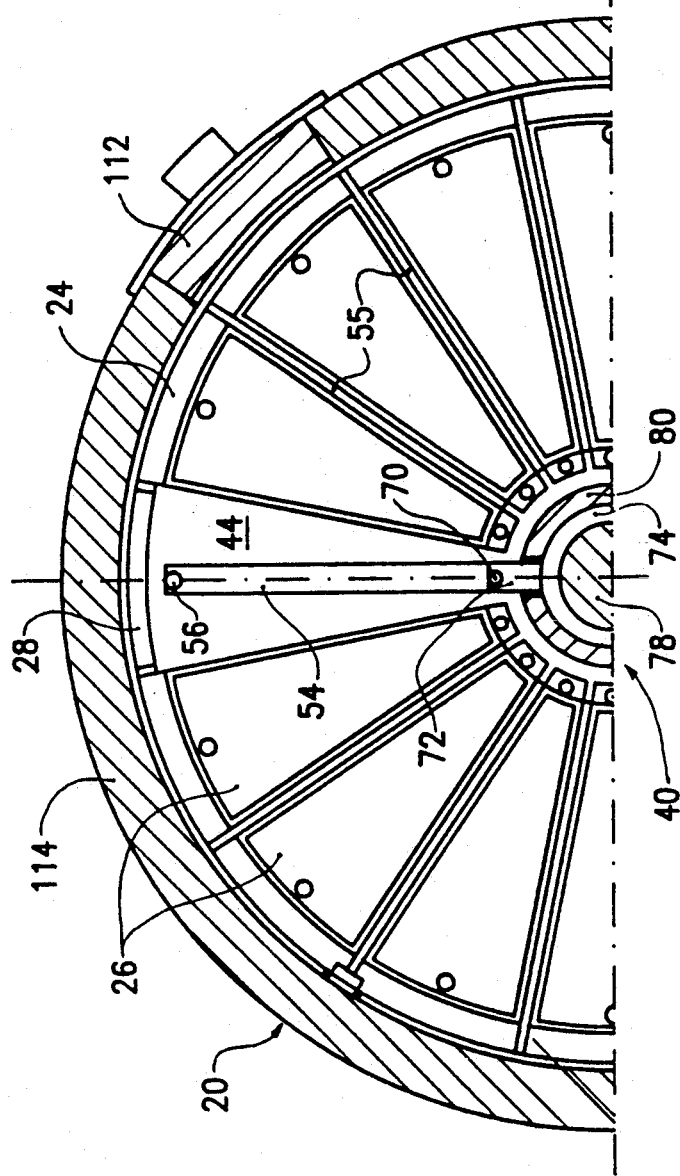
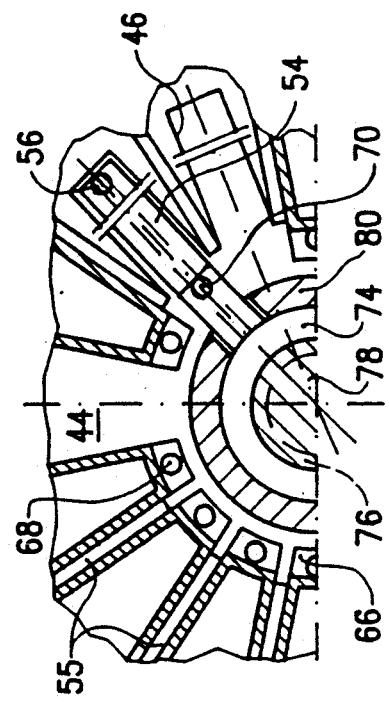
FIG.2
FIG.3

STORAGE APPARATUS, PARTICULARLY WITH AUTOMATIC INSERTION AND RETRIEVAL

BACKGROUND OF THE INVENTION

This invention relates to a storage apparatus. More particularly, this invention relates to an apparatus with automatic insertion and retrieval of samples from a storage container. More specifically, this invention relates to an apparatus for the preservation of biological specimens at various temperatures, including but not limited to the temperature of liquid nitrogen.

When properly treated, biological specimens can be stored almost indefinitely at temperatures approaching that of liquid nitrogen so long as that temperature is maintained. However, once the temperature of a specimen is raised, especially to a level where thawing occurs, the integrity of the specimen suffers if the specimen is then refrozen.

Many conventional cryogenic storage units are simple containers with removable racks having multiple shelves. Specimens are inserted and removed from the storage units manually through a door in the top of the unit. Retrieval operations always necessitate the removal of many specimens in the same rack as the desired specimen.

Such conventional cryopgenic storage units are inadequate for several reasons. Firstly, the storage temperature is not uniform and depends on the vertical location within the storage unit. Thus, some specimens may not be subjected to sufficiently low temperatures during storage. Secondly, the insertion and retrieval of specimens exposes many, if not all, of the stored specimens to ambient thawing temperatures, with a resultant decrease in the viability of the refrozen cells. Thirdly, ice crystals form on the specimens because of repeated exposure to the atmosphere during insertion and retrieval operations. This ice build up inhibits the reading of identification tags affixed to the specimens. In addition, the storage units are limited in their storage capacity because the units are generally no higher than the waist to facilitate manual insertion and retrieval operations.

U.S. Pat. No. 4,969,336 to Knippscheer et al. discloses a cryogenic storage device which corrects the abovementioned disadvantages of conventional cryogenic storage units. The device includes a pair of endless belts which move a multiplicity of specimen-containing vials along a snaking path. The locations of the vials within the unit are tracked by a computer which controls insertion and retrieval operations.

The cryogenic storage unit of U.S. Pat. No. 4,969,336, although superior to conventional cryogenic storage units which are manually operated, is subject to the disadvantage of having many moving parts. Such moving parts suffer from wear and thus require substantial repair and maintenance efforts.

OBJECTS OF THE INVENTION

An object of the present invention is to provide an improved storage unit, including but not limited to, a storage unit which is useful for low-temperature applications.

Another, more specific, object of the present invention is to provide a cryogenic storage unit wherein all the specimens are stored at essentially the same low temperature, regardless of the location of the specimens in the unit and regardless of ongoing insertion and retrieval operations.

A further object of the present invention is to provide a cyrogenic storage unit wherein ice crystal formation on the stored specimens is reduced, if not eliminated.

Another specific object of the present invention is to provide a storage apparatus wherein specimens or specimen-containing receptacles may be recovered or retrieved one at a time or in multiples, either automatically or manually.

Another object of the present invention is to provide a storage system with cross-checks for ensuring proper retrieval of requested samples.

Another specific object of the present invention is to provide such an apparatus wherein exposure of the specimens to temperatures above that of liquid nitrogen, especially thawing temperatures, is prevented.

Another object of the present invention is to provide a storage unit which has a reduced number of moving parts.

Another, more particular, object of the present invention is to provide a storage unit in which multiple storage receptacles or specimens may be inserted or removed simultaneously.

SUMMARY OF THE INVENTION

A storage unit comprises, in accordance with the present invention, a housing defining a storage chamber and a carrier inside the chamber for carrying, in a predetermined horizontal array, a plurality of specimens, for example, in storage receptacles. A rotary drive is operatively connected to the carrier for rotating the carrier about a vertical axis. The housing is provided with an access opening for enabling access to the chamber from above the carrier, while an insertion and removal mechanism serves to alternately insert and remove specimens from the chamber via the access opening.

Pursuant to another feature of the present invention, the insertion and removal mechanism includes an arm mounted outside the storage chamber. Pursuant to an additional feature of the present invention, the insertion and removal mechanism further includes a lifting device disposed at least partially inside the storage chamber for moving specimens vertically between the arm and the carrier. More specifically, the lifting device includes a carriage element and a drive member disposed vertically along an inner surface of the storage chamber for vertically reciprocating the carriage element. Alternatively, the drive member for the carriage element is disposed vertically along an axis of the storage chamber.

The specimens or specimen-containing receptacles are advantageously disposed on trays which in turn are supported by the carrier. In that case the lifting mechanism preferably operates to lift entire trays from the carrier towards the access opening to thereby cooperate with the arm to insert and remove specimens from the storage chamber.

Pursuant to another feature of the present invention, the insertion and removal mechanism includes an interchangeable adaptor for varying the number of specimens which can be inserted and removed from the storage chamber by the insertion and removal mechanism.

In accordance with another feature of the present invention, a second carrier or support is provided inside the storage chamber for carrying a second plurality of specimens, e.g., in storage receptacles. The second carrier is disposed to support the respective specimens or receptacles in a horizontal array parallel to the horizontal array of specimens supported by the first carrier. The rotary drive includes means for alternately rotating the first and the second carrier about the vertical axis of the storage unit. This function of the rotary drive enables selective insertion and removal of specimens relative to the different receptacle carriers.

A storage unit in accordance with the present invention automates the storage of specimens with simplicity. The storage unit contains a minimum of moving parts and thereby reduces repair and maintenance requirements.

Pursuant to another feature of the present invention, the rotary drive includes a drive member disposed axially with respect to the carrier and the storage chamber.

A storage unit in accordance with the present invention is particularly useful in low-temperature storage applications. Accordingly, the storage unit advantageously includes a cooling device for maintaining the storage chamber in a predetermined low temperature range. The cooling device preferably includes a circulating system for circulating a fluid coolant from a bottom portion of the storage chamber to an upper portion of the chamber above the carrier. Moreover, the circulating system includes a pump for drawing the fluid coolant from a sump in the bottom portion of the chamber. Where two carriers are disposed inside the storage chamber one above the other for carrying respective pluralities of specimens or specimen-containing storage receptacles in respective horizontal arrays, the two carriers are advantageously relatively disposed so that coolant runoff from the upper carrier falls to the lower carrier.

In accordance with a particular feature of the present invention, a sensor communicates with the sump for detecting ice build-up in the sump. Upon detection, the ice can be removed.

Pursuant to another feature of the present invention, a verification device is provided for confirming the identities of specimens being retrieved from the storage chamber.

Where the storage unit includes a cooling device for maintaining the storage chamber within a predetermined low temperature range, the storage unit may also comprise a hood or enclosure for defining a buffer chamber communicating with the storage chamber via the access opening during operation of the insertion and removal mechanism, whereby exposure of specimens to ambient temperatures is avoided.

Pursuant to another feature of the present invention, the storage unit further comprises at least one additional access opening for enabling access to the chamber laterally to the carrier. This additional opening may be of variable size to enable the removal of esepcially large specimens or of multiple receptacles or trays simultaneously.

A cryogenic storage unit built in accordance with the invention can store, in the same amount of space, substantially more vials than the storage unit of U.S. Pat. No. 4,969,336. In addition, repair and maintenance are facilitated in a storage unit in accordance with the invention, not only because malfunctions and breakdown may occur less frequently but also because access to the unit is simplified. Nothing can break which would have catastrophic consequences.

BRIEF DESCRIPTION OF THE DRAWING

FIG. 2 is a partial cross-sectional view taken along line II—II in FIG. 1.

FIG. 3 shows a detail of the crosss-sectional view of FIG. 2.

DETAILED DESCRIPTION

Figure 1:
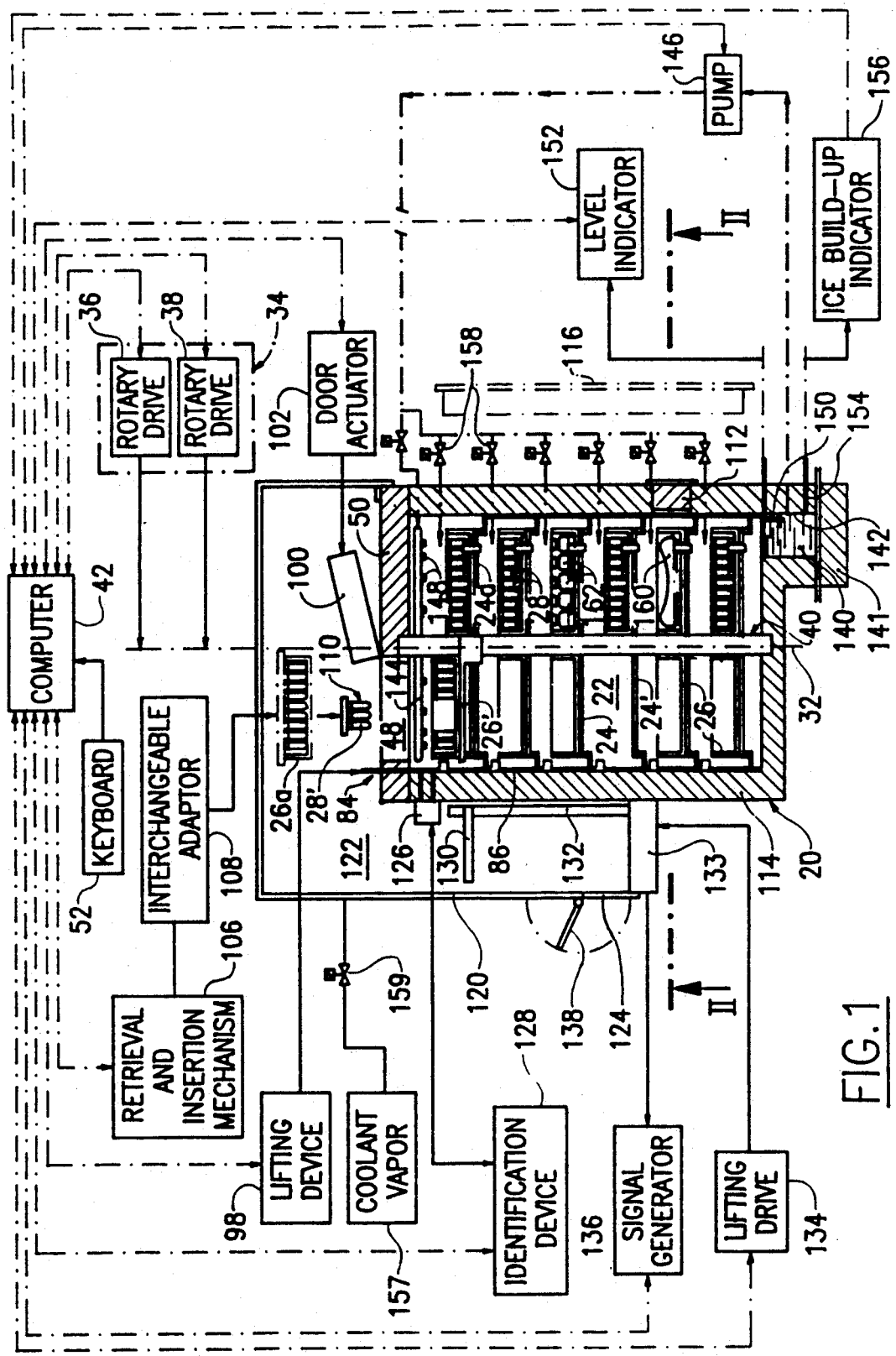
FIG. 1 is partially a schematic vertical cross-sectional view and partially a block diagram of a low-temperature storage apparatus in accordance with the present invention.

As illustrated in FIG. 1, a cryogenic storage apparatus comprises a cylindrical housing 20 defining a cylindrical storage chamber 22. Disposed inside storage chamber 22 are a plurality of substantially annular carriers or shelves 24. As shown in FIGS. 1 and 2, each shelf 24 supports a plurality of substantially triangular or pie-slice-shaped trays 26 which in turn carry a multiplicity of specimen-containing receptacles or vials 28. Vials 28 have been omitted from FIG. 2 for purposes of clarity.

Figure 4:
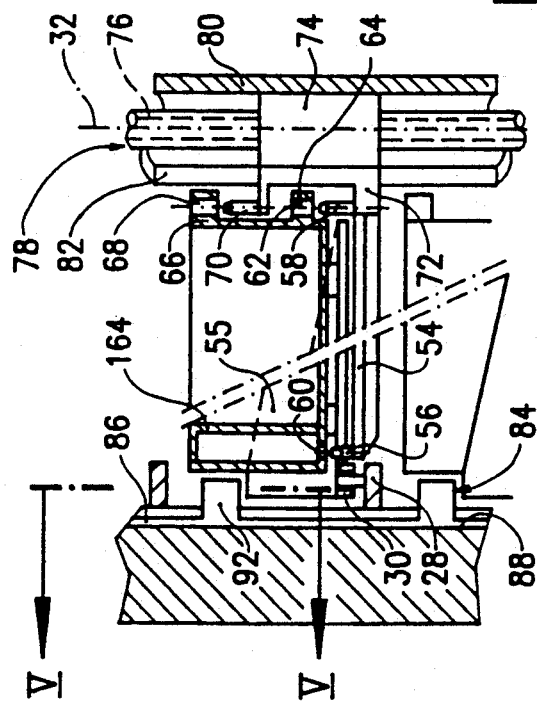
FIG. 4 shows a detail, on an enlarged scale, of the cross-sectional view of FIG. 1.
Figure 6:
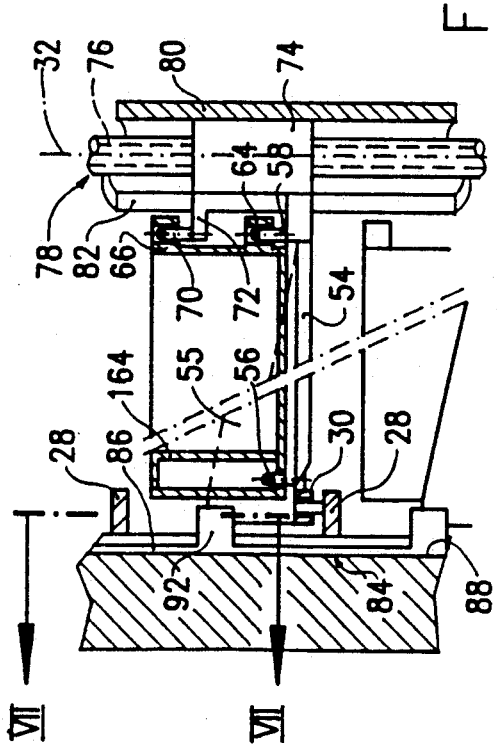
FIG. 6 is a view similar to FIG. 4, showing the low-temperature storage apparatus in a different stage of operation.

Shelves 24 are supported along their peripheries by respective annular rails or tracks 29 via respective annular bearings 30 (see FIGS. 2, 4 and 6). Rails 29 comprise respective rings with L-shaped cross-sections, each rail 29 resting on the rail below and supporting the rail above. This modular rail construction facilitates installation and repair procedures. Rails 29 may be formed with grooves (not shown) for receiving rollers (not shown) instead of bearings 30. This arrangement of rollers and grooves or some other horizontal guidance assembly is desirable to prevent shelves 24 from moving horizontally.

Shelves 24, together with their respective circular arrays of trays 26 and clusters of vials 28, are individually or independently rotatable about a vertical axis 32 by an axial and rotary drive mechanism 34. Drive mechanism 34 includes a pair of rotary drives 36 and 38 and an axial and rotary transmission assembly 40. In response to signals from a computer 42, rotary drives 36 and 38 operate transmission assembly 40 to alternately rotate selected shelves 24 about axis 32 and to vertically shift a selected tray 26 to and from a rotated shelf, as described in detail hereinafter.

As illustrated in FIGS. 2 and 3, shelves 24 are each formed with one triangular or pie-slice-shaped opening 44 and a plurality of angularly spaced radially extending slots 46. During operation of the cryogenic storage apparatus, openings 44 of all the shelves 24 are aligned vertically with an access opening or doorway 48 in a removable upper wall 50 of housing 20, as depicted in FIG. 1. Upon the determination by computer 42 (e.g., via a command or instruction fed to the computer via a keyboard 52) that access to a particular tray 26' (FIG. 1) is required, the shelf 24' carrying that selected tray 26' is rotated so that the tray is aligned with openings 44 of the other shelves 24 below doorway 48. The respective tray 26' is then elevated towards doorway 48 via a lifting arm 54 shown in FIGS. 2, 3, 4 and 6.

Lifting arm 54 is part of transmission assembly 40. FIG. 2 shows lifting arm 54 centered in an opening 44 of a shelf 24, while FIG. 3 shows lifting arm 54 centered in a slot 46. The purpose and function of the slots 46 in a shelf 24 are to enable arm 54 to traverse the shelf and lift the respective tray towards doorway 48. Accordingly, slots 46 are slightly larger than arm 54. Similarly, the purpose and function of openings 44 are to enable arm 54 to carry a selected tray 26' from its respective shelf 24' through overlying shelves 24.

As shown in FIGS. 2, 3, 4 and 6, shelves 24 are also provided with a plurality of vertically extending triangular reinforcement members 55. Each reinforcement member 55 bisects an angle defined by two adjacent slots 46. Concomitantly, each slot 46 bisects an angle defined by two adjacent reinforcement members 55.

As further shown in FIGS. 2, 3, 4 and 6, lifting arm 54 has a pair of upwardly extending pins 56 and 58 which are inserted through respective bores 60 and 62 in a selected tray (e.g., tray 26') during a vertical stroke of the lifting arm. The cooperation of pins 56 and 58 and bores 60 and 62 ensure that the selected tray 26' remains supported on arm 54 during vertical motion thereof between the respective shelf 24' and doorway 48.

Bore 62 is located in an eyelet extension 64 projecting from a narrow, radially inward side of the respective tray 26. As shown in FIGS. 4 and 6, each tray 26 is provided with lower eyelet extension 64 and an upper eyelet 66 which has a bore 68 for receiving an additional alignment pin 70. Pin 70 and bore 68 serve the same function as pins 56 and 58 and bores 60 and 62.

As illustrated in FIGS. 4 and 6, pin 70 is attached to a vertically oriented flange 72 projecting from a collar 74. Flange 72 and collar 74 form a portion of transmission assembly 40. Collar 74 is formed with an internal screw thread (not illustrated) which is operatively interleaved with an external screw thread 76 of a rotatable shaft 78. Shaft 78 is driven by rotary drive 36 under the control of computer 42.

Shaft 78 and collar 74 are coaxial with a rotatable tube 80 which is provided with a vertical slot 82 traversed by flange 72. Tube 80 is rotated by drive 38 in response to control signals from computer 42.

When rotary drives 36 and 38 are rotating together at the same angular velocity, collar 74, flange 72 and lifting arm 54 maintain the same elevation and rotate about axis 32, thereby driving an entrained shelf (e.g., shelf 24') in a horizontal plane. When rotary drive 38 is disengaged or de-energized while drive 36 continues to rotate shaft 78, collar 74, flange 72 and lifting arm 54 maintain the same angular position and move vertically, thereby lifting or lowering a selected tray (e.g., tray 26'), depending on the direction of rotation of shaft 78.

Other rotating and lifting mechanism equivalent to drive mechanism 34 takes the form of a plurality of motors (not illustrated) mounted, for example, to housing 20 and operatively coupled to respective shelves 24 via respective rack and pinion transmissions (not illustrated). The racks in that case are annular elements attached to shelves 24 at the circumferences thereof. The lifting may be accomplished by an elevation mechanism disposed along an inner surface of housing 20, as described hereinafter with reference to FIG. 12. A disadvantage of this rotating and lifting mechanism is an undesirable duplication of parts, particularly motors and transmissions. However, it may be desirable, to have an uppermost carrier or shelf alternatively drivable by a separate motor (not illustrated) so that that shelf can serve as a temporary storage location during rearrangements of stored vials.

In another rotating and lifting mechanism equivalent to drive mechanism 34, both rotating and lifting functions are accomplished by a central rotary drive shaft (not illustrated) which is axially reciprocatable. The lower, free end of the shaft is formed with a flange of an irregular shape keyed to similarly shaped openings in the centers of the carriers or shelves. In this equivalent embodiment of the rotating and lifting mechanism, the computer controls the orientation of the drive shaft so that the shaft passes through the openings of unselected carriers during vertical reciprocation of the shaft. At a selected carrier, the shaft is turned, e.g., 90°, so that the irregular flange cannot pass through the opening in the center of the selected carrier. Raising the shaft thus lifts the carrier. Rotation of the carrier can be effectuated by slowly turning the shaft while the selected carrier is supported on the irregular flange. A disadvantage of this embodiment of the rotating and lifting mechanism is that a clearance essentially equal to the length of the shaft must be available above the cryogenic storage unit, thereby limiting the utilizable height of the unit.

Figure 5:
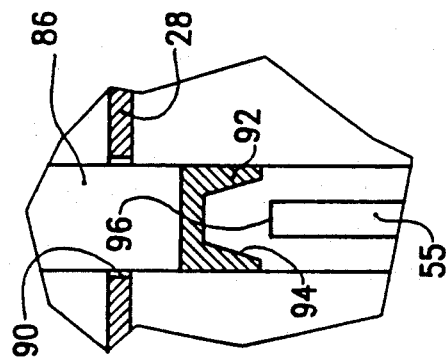
FIG. 5 is a partial cross-sectional view taken along line V—V in FIG. 4.
Figure 7:
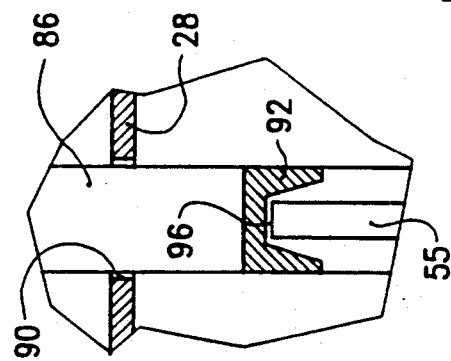
FIG. 7 is a partial cross-sectional view taken along line VII—VII in FIG. 6.

As illustrated in FIGS. 1 and 4–7, the cryogenic storage unit is provided with a locking mechanism 84 including a vertically shiftable rod 86 disposed along an inner surface 88 of housing 20. Rod 86 traverses slots 90 provided in support rails 29 and is provided with a plurality of vertically spaced locking plates 92. As shown in FIGS. 5 and 7, locking plates 92 are formed with respective slots 94 for receiving upper edges 96 of respective reinforcement members 55.

As shown in FIG. 1, rod 86 is operatively coupled to a lifting device 98 which may take the form of a solenoid or a pneumatic or hydraulic cylinder which is energized or actuated under the control of computer 42. Prior to the rotation of shelf 24', lifting device is actuated to lift rod 86 and thereby disengage slotted locking plates 92 and reinforcement members 55. During rotary motion of a selected shelf under the action of drive mechanism 34, lifting device 98 remains actuated and rod 86 remains shifted. Upon termination of the rotary motion, lifting device is deactuated by computer 42, thereby returning rod 86 and slotted locking plates 92 to the locking position engaging shelves 24 and 24'.

It is to be noted that other locking mechanisms equivalent to locking mechanism 84 are readily available to one skilled in the art. For example, housing 20 may be provided along inner surface 88 with a plurality of vertically spaced electromagnets (not illustrated) individually controlled by computer 42 to magnetically attract and fix shelves 24 and 24'.

As further illustrated in FIG. 1, housing 20 is provided on upper wall 50 with a swingable or slidable door 100 for closing doorway or access opening 48. Door 100 is alternately opened and closed by a robot mechanism or actuator 102 under the control of computer 42. The cryogenic storage apparatus is also provided with a retrieval and insertion mechanism 106 for alternatively retrieving and inserting vials 28 and clusters 110 of vials 28 into housing 20. Retrieval and insertion mechanism 106 thus cooperates with lifting arm 54 and its associated axial and rotary drive mechanism 34 in the placement and removal of specimens from the cryogenic storage unit.

Retrieval and insertion mechanism 106 is provided with an interchangeable adaptor 108 for enabling a variation in the number of specimens which can be transfered simultaneously by retrieval and insertion mechanism 106. The adaptor includes snap locking elements, electromagnets, hook and eyelet components or other devices (not shown) for enabling the attachment of different grasping components (not shown). The different grasping components respectively manipulate single vials, vial clusters 110 or an entire tray 26a.

Entire trays may alternatively be removed or inserted into housing 20 via an an access opening or door 112 (FIGS. 1 and 2) in a sidewall 114 of the housing. Sidewall 114 may be provided with a column (not shown) of such openings to enable access to each shelf 24. Alternatively, sidewall 114 may be provided with a single doorway 116 variable in height and width.

As also shown in FIG. 1, the storage apparatus is provided with a removable hood or cover member 120 defining an antechamber 122 which communicates with storage chamber 22 upon an opening of door 100. During use of the apparatus, the opening of door 100 enables coolant vapors from storage chamber 22 to penetrate into antechamber 12 and drive out ambient air through an aperture 124 at the base of hood 120. Antechamber 122 is thereby substantially filled with coolant vapor, minimizing the formation of ice crystals on cooled samples, particularly on vials 28.

Upon receiving from keyboard 52 an order to retrieve a vial 28' stored in housing 20, computer 42 energizes rotary drive 36 while maintaining drive 38 in a disengaged or de-energized state to first shift collar 74, flange 72 and lifting arm 54 in a vertical direction to a vertical position slightly below the shelf 24' holding the selected vial 28'. During this vertical shifting, collar 74, flange 72 and lifting arm 54 pass through openings 44 in shelves 24.

Upon the attainment of the desired vertical position by collar 74, flange 72 and lifting arm 54, computer 42 engages both rotary drives 36 and 38 to rotate lifting arm 54 so that it is vertically aligned with the slot 46 associated with the tray 26' holding the selected vial 28'. Rotary drive 36 is then engaged while rotary drive 38 is de-energized to vertically elevate lifting arm 54 through the slot 46 and slightly above the level of the respective shelf 24'. Lifting device 98 is then actuated in response to signals from computer 42 to raise rod 86 and unlock shelves 24 and 24'. At that point, both rotary drives 36 and 38 are operated under the control of computer 42 to rotate the selected shelf 24' so that the tray 26' carrying the selected vial 28' is aligned vertically with openings 44 and below doorway 48. Then locking mechanism 84 is operated to again lock shelves 24 and 24' in stationary positions, while rotary drive 38 is disengaged, so that subsequent operation of drive 36 causes collar 74, flange 72 and lifting arm 54, as well as the tray 26' carried thereby, to rise towards doorway 48 through openings 44 in the overlying shelves 24.

Upon the tray's attainment of a predetermined vertical position in juxtaposition to doorway 48, drive 36 is also disengaged. Computer 42 then activates robot mechanism or actuator 102 to open door 100. Upon the opening of door 100, retrieval and insertion mechanism 106 is operated to extract the selected vial 28' (or selected vial cluster or tray) from housing 20.

Sidewall 114 of housing 20 is provided at doorway 48 with an optical scanner 126 for reading, during insertion and retrieval operations, bar code labels (not shown) attached to the vials being inserted and/or retrieved from storage chamber 22. During the removal of selected vial 28' from housing 20, an identification device 128 connected to optical scanner 126 and computer 42 verifies the identity of the retrieved vial 28' (or group of vials) to computer 42. It is to be noted that the verification of vial or specimen identities may be implemented via different types of sensors, such as infrared sensors, tactile detectors, holographic devices or acoustic sensors. The operation of identification device 128 and scanner 126 is described in U.S. Pat. No. 4,969,336, the disclosure of which is incorporated by reference herein.

Upon verification of the identity of the retrieved vial 28', retrieval and insertion mechanism 106 lowers the vial into or onto a holder 130 which reciprocates along a vertical track or rail 132 under the control of a lifting drive 134. Upon the deposition of retrieved vial 28' into holder 130, computer 42 signals lifting drive 134 to lower the holder into a temporary holding chamber o enclosure 133 juxtaposed to aperture 124 at the lower end of rail 132. Upon the arrival of holder 130 at enclosure 133, a signal generator 136 produces preferably an audible tone for alerting an operator that the requested vial has been retrieved and is available in enclosure 133. A door 138 Covering aperture 124 is hinged to hood 120 and may be manually pivoted to enable access to antechamber 122. Signal generator 136 may be activated by a sensor (not illustrated) in enclosure 133 or may be activated by computer 42 upon a determination thereby that holder 130 has reached enclosure 133.

Storage chamber 22 and particularly the vials 28 contained therein are maintained at a substantially predetermined low temperature by a liquid coolant 140 which is circulated from a sump 142 at the bottom of chamber 22 to a distribution ring or manifold 144 by a pump 146. Distribution ring 144 is disposed at the top of chamber 22 above an uppermost shelf 24a. Coolant 140, which is preferably liquid nitrogen, is discharged through nozzles 148 in ring 144 and falls into trays 26 carried by shelf 24a. Subsequently, the coolant cascades from shelf to shelf (level to level) down through chamber 22. Preferably, the liquid coolant cascades from tray to underlying tray.

A sensor 150 communicates with sump 142 and is connected to a level indicator 152. In the event that the level of liquid nitrogen in sump 142 is below a predetermined level, indicator 152 opens a valve (not illustrated) to allow liquid nitrogen to flow from a reservoir (not shown) to sump 142. After the nitrogen level in sump 142 rises to another predetermined level, indicator 152 closes the valve, thereby preventing further nitrogen flow from the reservoir to the sump. Level indicator 152 issues an alert signal in the event that the valve is malfunctioning and generates an alarm if the level of liquid nitrogen in sump 142 rises above a third predetermined level higher than the first two levels.

An additional sensor 154 is provided at the bottom of sump 142 for detecting the presence of ice build-up in the sump. Sensor 154 is operatively connected to an indicator 156 which generates a signal to alert an operator as to the presence and possibly extent of ice build-up in sump 42. Ice can be manually removed through a door or flange 141 at sump 142.

As shown in FIG. 1, pump 146 may be connected on an outlet or downstream side to a plurality of valves 158 for controlling the flow of liquid coolant to respective shelves 24 in an alternative low-temperature operation of the storage apparatus. Thus, the coolant may be circulated by pump 146 between sump 142 and the trays 26 on the different shelves 24. Pump 146 also serves to add liquid coolant from a reservoir (not shown) to the supply inside chamber 22 and to maintain the low temperature of the coolant, if necessary, by moving the coolant through a heat exchanger (not illustrated).

In the event that the coolant used in chamber 22 has a boiling point higher than room temperature and does not vaporize to fill antechamber 122, another gas may be used to evacuate that chamber of ambient air (particularly water vapor, which forms ice crystals on the vials). The additional may be nitrogen gas, carbon dioxide or other gas and is stored in a reservoir 157 which communicates with antechamber 122 via a valve 159. Valve 159 and valves 158 are operated by computer 42. Connecting leads between computer 42, on the one hand, and valves 158 and 159, on the other hand, have been omitted from the drawing for purposes of clarity.

As shown in FIG. 1, the low-temperature storage apparatus may be used to store large specimens such as entire organs 160 and containers 162 of different sizes.

Figure 8:
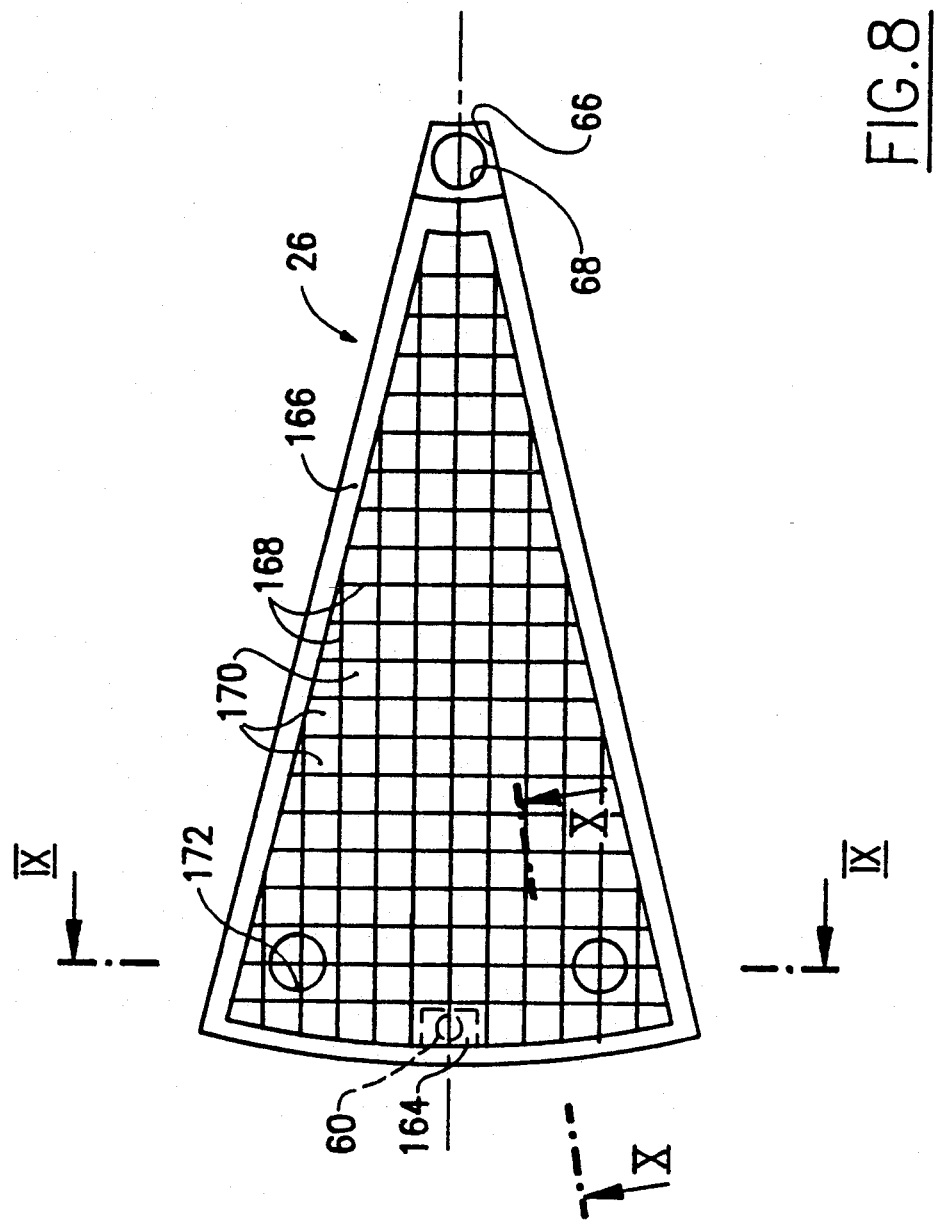
FIG. 8 is a top or plan view of a tray held on a shelf inside the storage apparatus of FIG. 1.

FIG. 8 is a top or plan view of a tray 26 held on a shelf 24 inside storage chamber 22. As discussed hereinabove with reference to FIGS. 4 and 6, tray 26 is provided at opposite ends with bores 60 and 68 for receiving alignment and support pins 56 and 70 on lifting arm 54 and flange 72. Bore 60 may be provided with a cover 164 (see also FIGS. 4 and 6) for preventing the inadvertant placement of a vial into bore 60.

As shown in FIG. 8, tray 26 has a peripheral wall 166 of substantially triangular shape and is provided with intersecting partitions 168 to define a multiplicity of prismatic receptacles 170 for vials 28. Partitions 168 are removable so that they may be replaced with substitute partitions (not shown) which define receptacles (not shown) of a size or shape different from the size and shape of receptacles 170. Tray 26 is formed with at least one opening 172 in a bottom wall 174 (see also FIG. 9) for enabling a quick release of all liquid coolant in the tray upon an elevation of the tray by lifting arm 54 during a retrieval operation.

Figure 9:
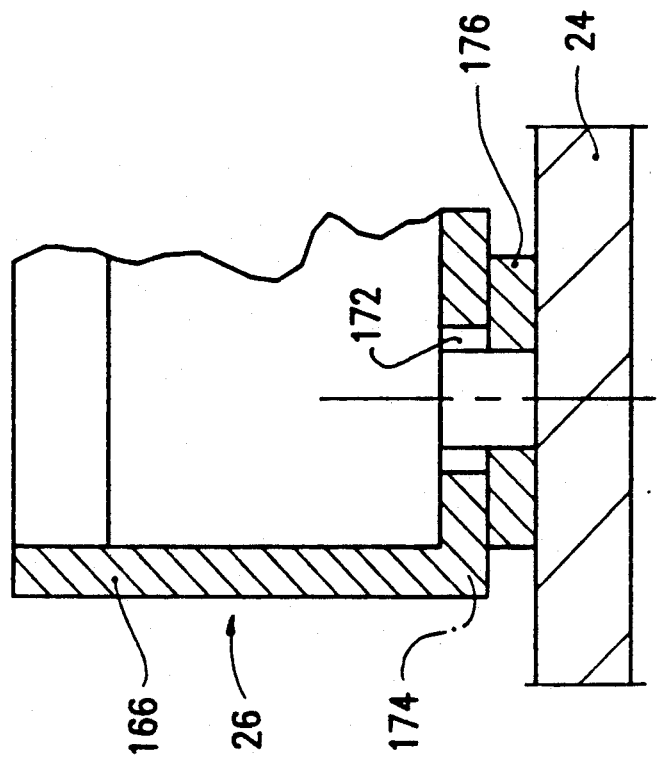
FIG. 9 is a partial cross-sectional view taken along line IX—IX in FIG. 8.

As depicted in FIG. 9, a ring-shaped sealing gasket 176 is disposed between bottom wall 174 of tray 26 and shelf 28 on which tray 26 rests during storage. Gasket 176 is preferably fastened to the lower surface of bottom wall 174. For purposes of simplicity, it is to be noted that FIGS. 9 and 10 omit depiction of partitions 168 and receptacles 170.

Figure 10:
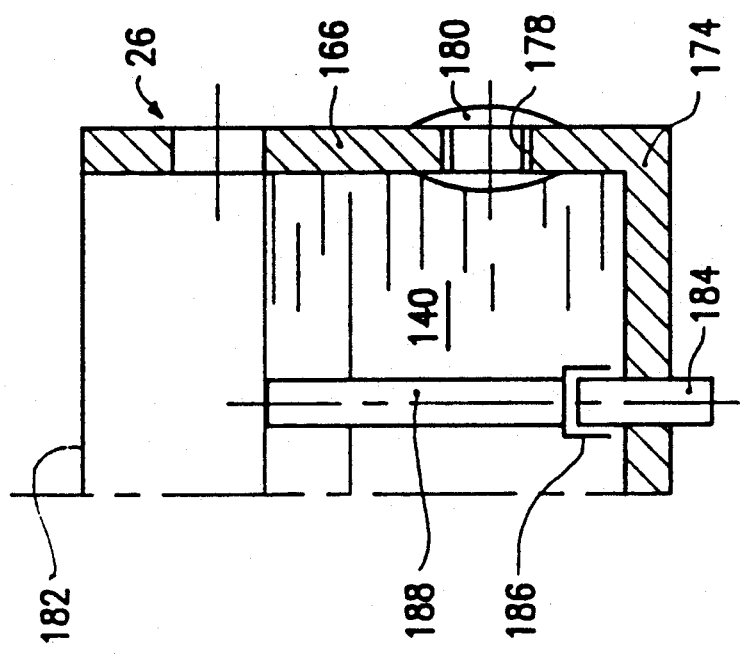
FIG. 10 is a partial cross-sectional view taken along line X—X in FIG. 8.

FIG. 10 illustrates two alternative methods of varying the amount of liquid coolant 140 held inside a tray 26. As shown to the left of that drawing figure, bottom wall 174 may be provided with one or more tubular fittings 184. Fitting 184 is positioned so that liquid coolant from the tray 26 falls through the fitting 184 to an underlying tray. A tube or pipe 188 is provided with a collar 186 which mates with an upper end of tubular fitting 184 to form a substantially fluid-tight seal. Pipe 188 has a preselected length so that the pipe, when placed atop fitting 184, extends to a predetermined desired coolant level 182. Level 182 is selected in the event, for example, that storage containers 162 (FIG. 1) are so large as to require additional coolant to adequately maintain the containers and their contents at a desired low storage temperature. Generally, however, it is to be noted that only a very mimimum level of liquid coolant (e.g., nitrogen) is necessary in the bottoms of trays 26 to maintain receptacles or vials 28 and their contents at a desired low storage temperature.

As an alternative or supplement to fittings 184 and pipes 188, peripheral wall 166 is formed with a plurality of apertures 178 at different distances from bottom wall 174. Apertures 178 below the desired coolant level 182 in tray 236 are closed with respective sealing plugs 180.

Figure 11:
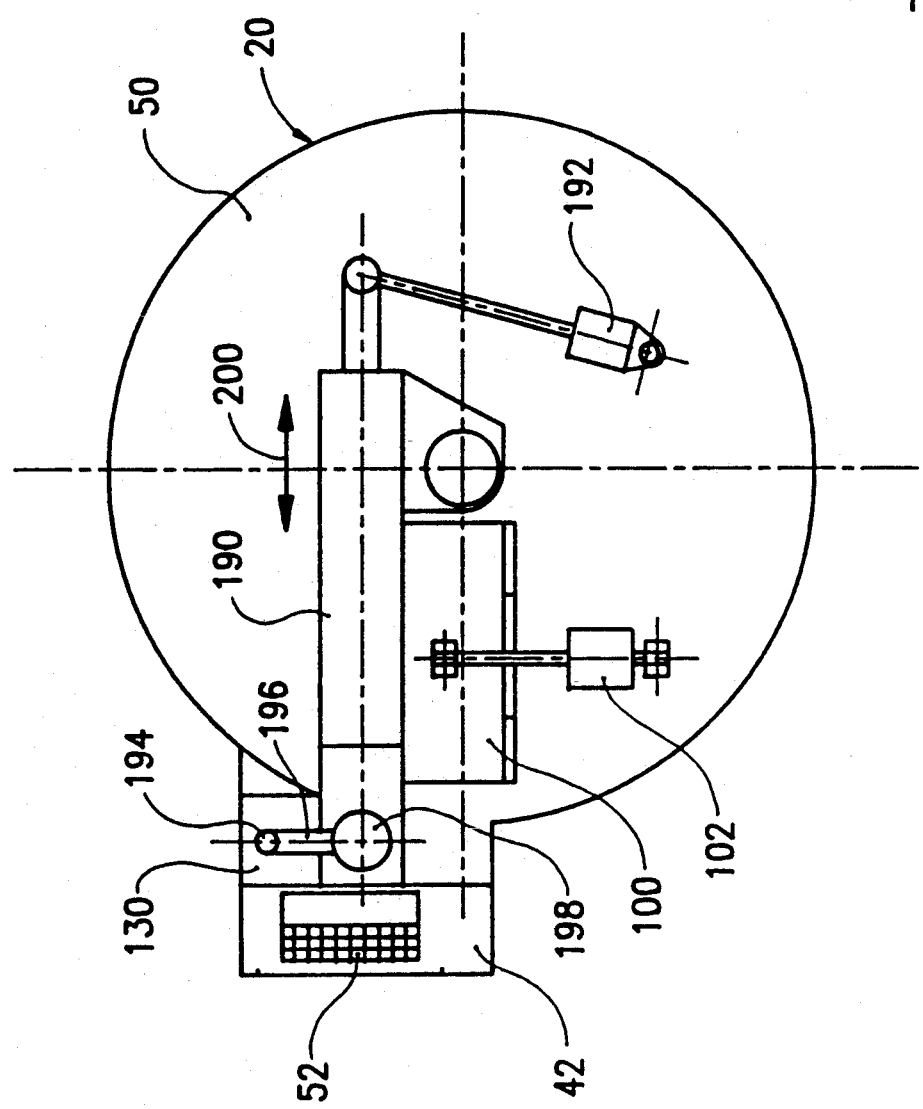
FIG. 11 is a partial top view of the storage apparatus of FIG. 1, showing a portion of an retrieval and insertion mechanism.

FIG. 11 depicts a possible implementation of retrieval and insertion mechanism 106 (FIG. 1) and also shows robot mechanism or actuator 102 and door 100, as well as keyboard 52 mounted to sidewall 114. Retrieval and insertion mechanism 106 includes an arm 190 rotatably mounted at axis 32 (FIG. 1) to upper wall 50 and pivoted by an electromagnetic, pneumatic or hydraulic actuator 192 mounted to housing wall 50. Actuator 192 operates under the control of computer 42. At the free end of arm 190 is disposed a grasping element 194 preferably in the form of an electromagnet, as described in U.S. Pat. No. 4,969,336 which is incorporated by reference herein. The electromagnet may be mounted to the lower end of a telescoping member (not shown) or a rack member (not shown) driven by a pinion (not shown). The telescoping member or rack member is in turn mounted to the free end of an auxiliary arm 196 pivotably attached to primary arm 190. Auxiliary arm 196 is rotated by a motor 198 controlled by computer 42. Grasping element or electromagnet 194 is also shiftable longitudinally along arm 190 in a direction indicated by an arrow 200.

Figure 12:
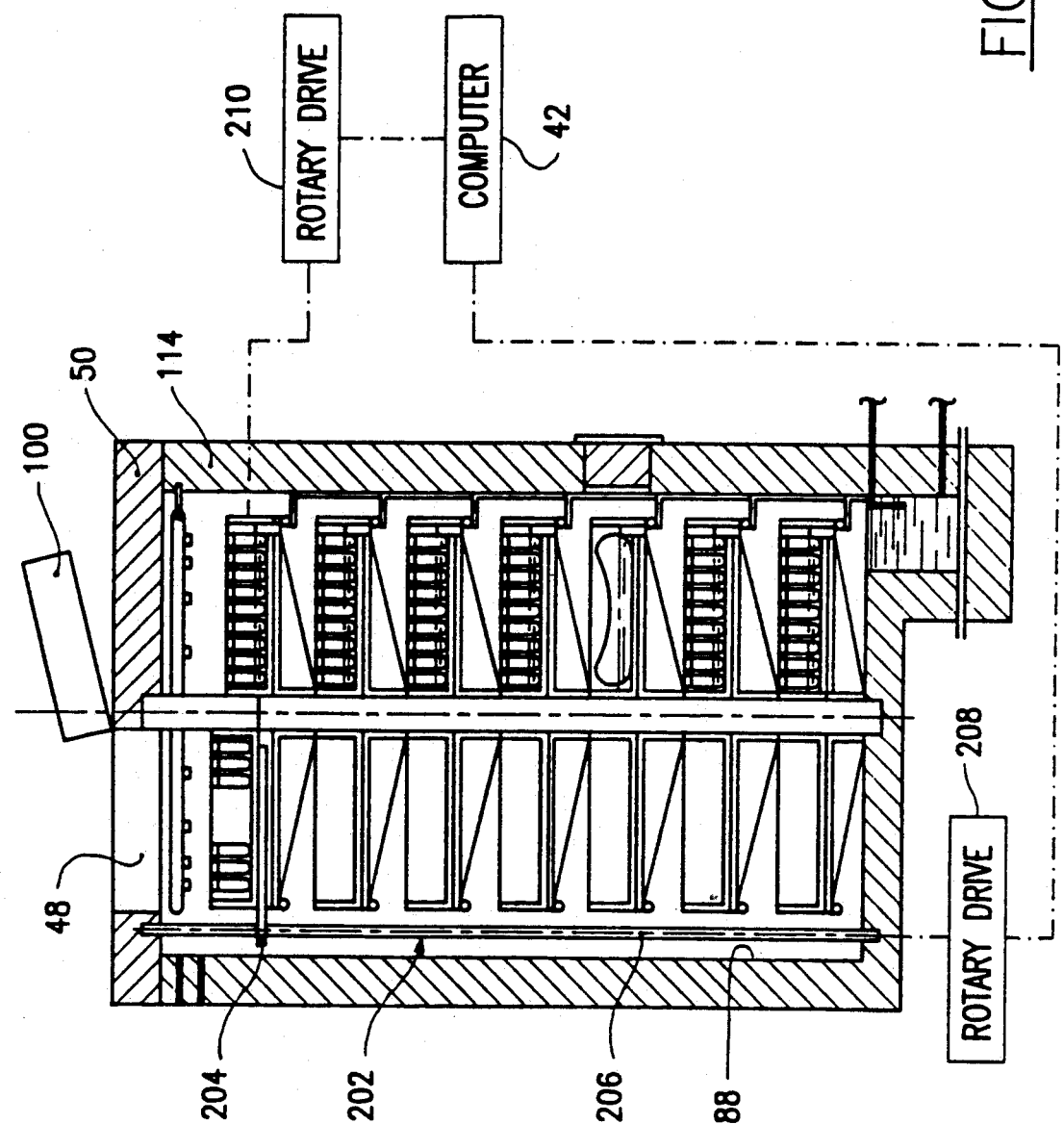
FIG. 12 is a schematic vertical cross-sectional view of another low-temperature storage apparatus in accordance with the present invention.

FIG. 12 shows an alternative embodiment of axial and rotary drive mechanism 34 (FIG. 1). In the embodiment of FIG. 12, the elevation of the trays 26 to doorway 48 is accomplished by a lifting mechanism 202 disposed along inside surface 88 of housiong sidewall 114. Lifting mechanism comprising a lifting arm 204 shiftably mounted to a rotatable rod or shaft 206 extending vertically along sidewall 114. Rod or shaft 206 is rotated by a rotary drive 208 under the control of computer 42. As discussed hereinabove with reference to FIGS. 1-4 and 6, rod or shaft 206 is externally threaded and drivingly mates with an internally threaded portion (not designated in the drawing) of lifting arm 204. An arrest similar to slot 82 of tube 80 may be provided for preventing the rotating of arm 206 and for concomitantly constraining the arm to one degree of freedom of movement, i.e., in the vertical direction. The rotation of shelves 24 is accomplished in the same manner as discussed hereinabove, except that flange 72 rather than lifting arm 54 fits into slots (not shown) provided in shelves 24. Alternatively, as discussed hereinabove, shelves 24 may be rotated by another, equivalent method such as separate motors operatively coupled to the shelves by rack and pinion step-down transmissions.

As described in U.S. Pat. No. 4,969,336, the storage apparatus disclosed herein is provided with various sensors for enabling computer 42 to monitor the state of rotation of shelves 24 and thus the locations of trays 26 and of vials 28. Temperature sensors and other feedback devices may also be incorporated. Temperatures sensors would be positioned, for example, in one or more trays 26 on each shelf 24 and would transmit temperature-encoding signals to computer 42 via brushes and slip rings on shelves 24 and rails 29.

In operation, computer 42 may be required to retrieve a number of vials 28 which are stored throughout chamber 22, in different trays 26 and on different shelves 24. Such a procedure may be required, for example, in the event that the computer 42 is instructed to collect multiple specimens all characterized by a particular feature (e.g., common blood type) communicated to computer 42 via keyboard 52. To enable computer 42 to efficiently implement such a procedure, uppermost shelf 24 is preferably rotated by a separate drive, for example, a rotary motor 210 (see FIG. 12) mounted to sidewall 114 at the upper end thereof. Motor 210 is controlled by computer 42 so that shelf 24a may be used as a temporary storage location or buffer. Because shelf 24a is rotated separately from the other shelves 24 and because retrieval and insertion mechanism 106 (FIG. 1) may be used in cooperation with shelf 24a independently of drive 34 and transmission 40, reorganization of stored vials 28 is facilitated. For example, several vials 28 may be removed from the same tray 26' (FIG. 1) and placed in a temporary storage tray (not designated) on shelf 24a, without it being necessary for tray 26' to be removed more than a small distance from access opening 48. Without the separate drive for shelf 24a, it would be necessary for drive 34 to move tray 26' back to shelf 24' each time a vial 28 was taken from tray 36' by retrieval and insertion mechanism 106.

Figure 13:
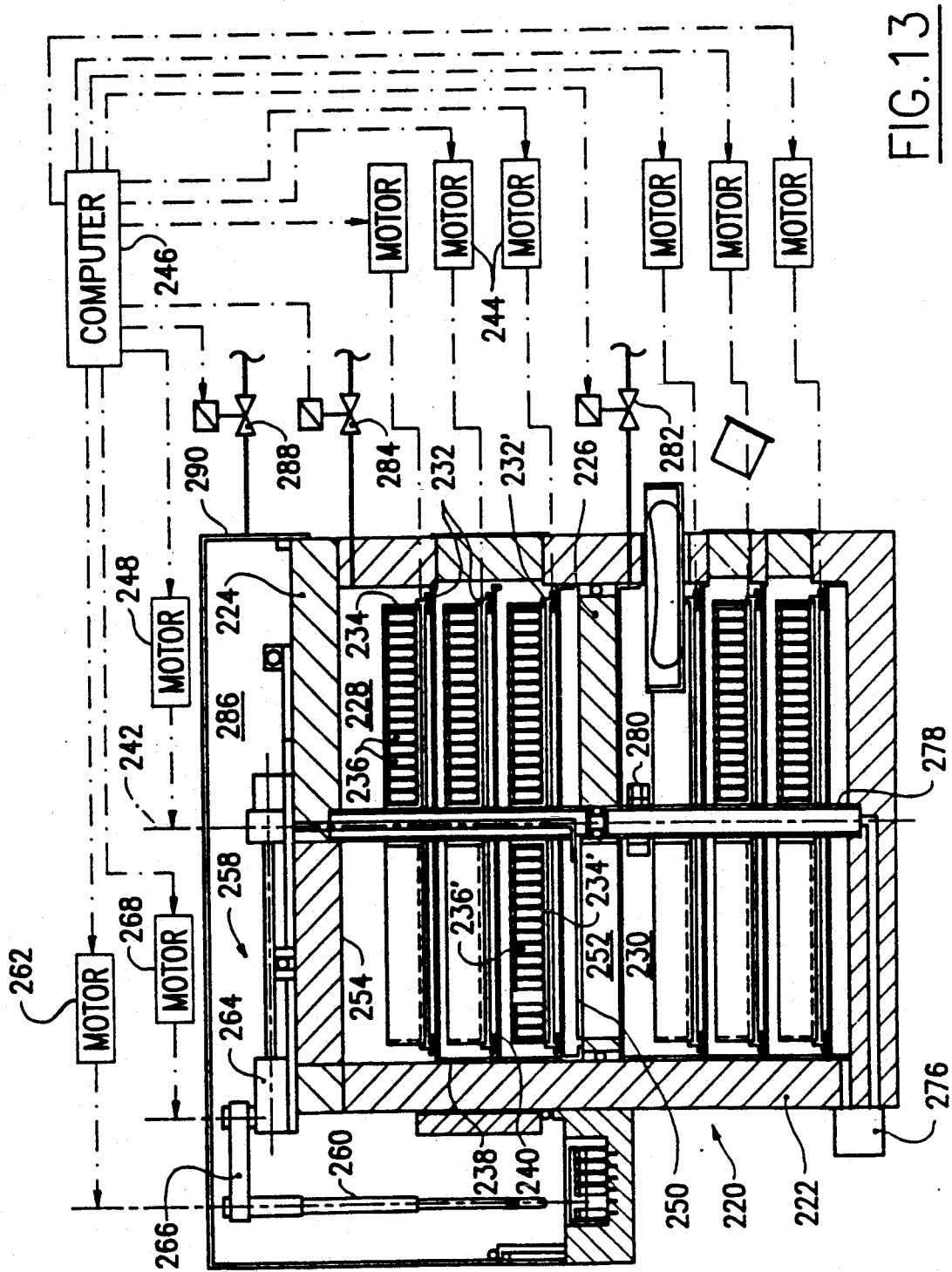
FIG. 13 is partially a schematic vertical cross-sectional view and partially a block diagram of another low-temperature storage apparatus in accordance with the present invention.
Figure 14:
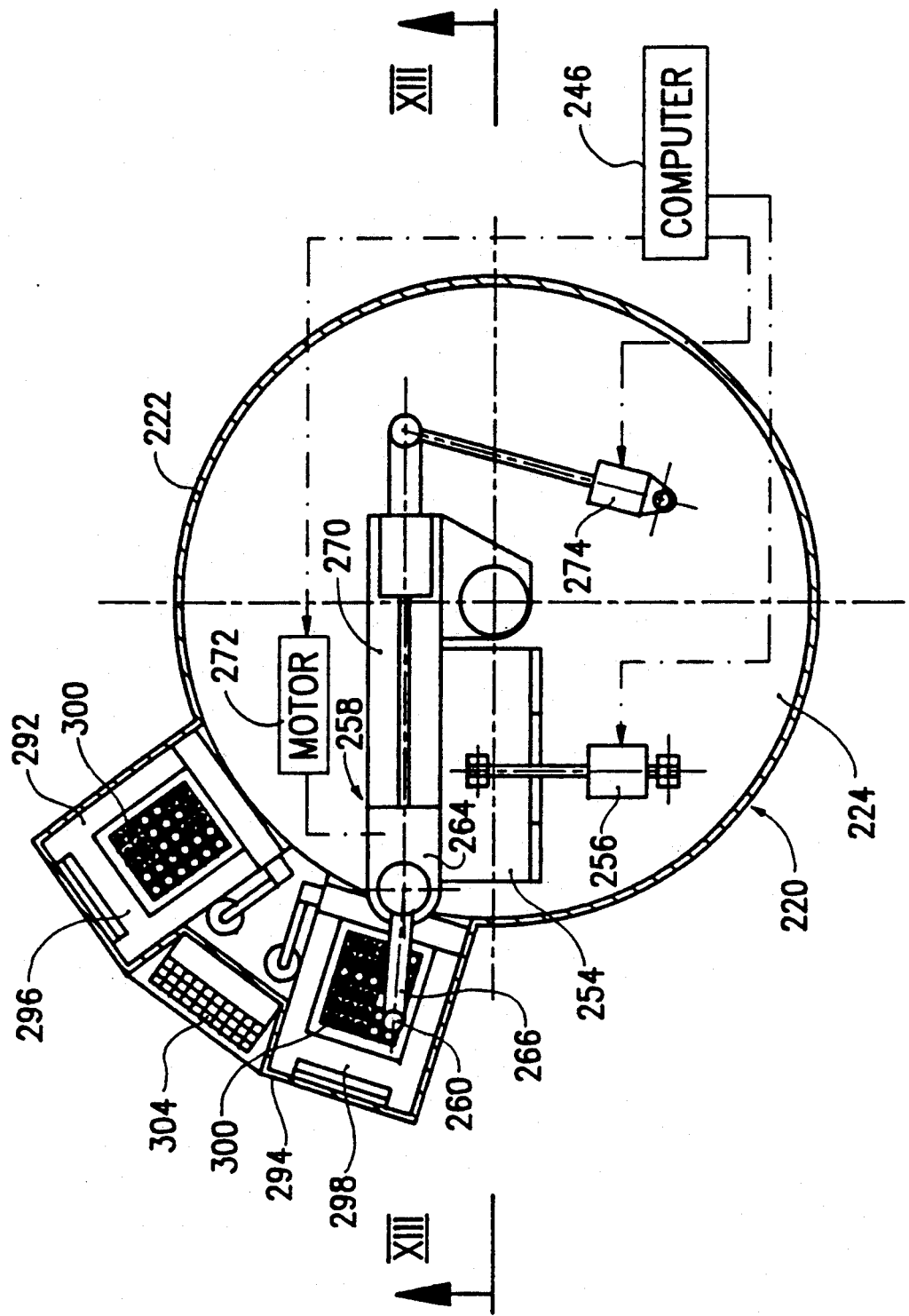
FIG. 14 is a top view of the storage apparatus of FIG. 13.

As illustrated in FIGS. 13 and 14, another low-temperature storage apparatus comprises a housing 220 with a sidewall 222, a top wall 224 and a partition 226 defining a pair of vertically aligned storage chambers 228 and 230. Disposed inside each storage chamber 228 and 230 are a plurality of substantially annular carriers or shelves 232. As described hereinabove with reference to FIGS. 1 and 2, each shelf 232 supports a plurality of substantially triangular or pie-slice-shaped trays 234 which in turn carry a multiplicity of specimen-containing receptacles or vials 236.

Shelves 232 are supported along their peripheries by respective annular rails or tracks 238 via respective annular bearings 240. Rails 238 comprise respective rings with L-shaped cross-sections, each rail 238 resting on the rail below and supporting the rail above. Rails 238 may be formed with grooves (not shown) for receiving rollers (not shown) instead of bearings 240. This arrangement of rollers and grooves or some other horizontal guidance assembly is desirable to prevent shelves 232 from moving horizontally.

Shelves 232, together with their respective circular arrays of trays 234 and clusters of vials 236, are individually or independently rotatable about a vertical axis 242 by a respective rotary drives or motors 244. Motors 244 are energized under the control of a computer 246 which also controls a motor 248 pivoting about axis 242 a door 250 covering an opening 252 in partition 226.

As described hereinabove with reference to FIGS. 1–4 and 6, each shelf 232 is provided with an opening or cutout (not labeled) which are alignable with each other and with an access door 254 in upper wall 224. Upon the selection of a vial 236' to be removed, the shelf 232' supporting that vial is rotated by its respective motor 244' to a position so that a tray 234' carrying the vial 236' is aligned beneath door 250. Upon the opening of door 250 by an actuator 256 (FIG. 14), a retrieval and insertion mechanism 258 is operated by computer 246 to retrieve the selected vial 236' from its tray 234'.

As illustrated in FIG. 13, retrieval and insertion mechanism 258 may include a telescoping arm 260 extendable by a motor 262 under the control of computer 246 and pivotably linked to a carriage 264 via a rotatable lever arm 266. Lever arm 266 is rotated by a motor 268 under the control of computer 246, while carriage 264 is shifted along a track 270 by another motor 272. Track 270 is itself pivotable about axis 242 by an actuator 274.

It is contemplated that telescoping arm 260 has a sifficient extension to reach to the lowermost sehlf in lower cooling chamber 230. However, it is also within the contemplation of the invention that retrieval and insertion mechanism 258 may comprise a lifting arm similar, for example to that discussed hereinabove with reference to FIG. 1 or FIG. 12. In that case, telescoping arm 260 need not have so great an extension.

Chamber 230 is cooled by liquid coolant such as liquid nitrogen which is pumped by a pump 276 vertically through an axially disposed pipe 278 to a central distribution ring or manifold 280. The liquid nitrogen then cascades from shelf to underlying shelf as described hereinabove with reference to the embodiment of FIG. 1.

Alternatively chamber 230 may be cooled with a gaseous coolant at one temperature while chamber 228 is cooled by a gaseous coolant at a second, higher temperature. The coolants flow from respective reservoirs (not illustrated) under the control of valves 282 and 284 responsive to signals from computer 246. The gaseous coolant may be the same gas (e.g., vaporous nitrogen) cooled to different temperatures. Storage chambers 228 and 230 can thus store specimens requiring different temperature ranges for long term storage.

Another gas is fed to an antechamber 286 via a computer controlled valve 288 to evacuate moisture. Antechamber 286 is defined by a hood 290 over the top of housing 220.

Disposed at a lower end of chamber 286, at about waist level, is a pair of enclosures 292 and 294 defining a thawing chamber 296 and a freezing chamber 298. Thawing chamber 292 operates to bring specimens from the respective long-term storage temperature (the temperature of chamber 228 or chamber 230) to ambient temperatures, while freezing chamber 294 serves to bring specimens from the ambient temperatures to the preselected long-term storage temperature (the temperature of chamber 228 or chamber 230). FIG. 14 shows a pair of trays 300 and 302 inside chambers 296 and 298. A keyboard 304 connected to computer 246. It is contemplated that computer 246 is physically juxtaposed to keyboard 304, below it.

Thawing chamber 296 and freezing chamber 298 can be operated to thaw and freeze specimens at different, varying rates, in accordance with variable protocols depending on the nature of the specimens.

Although the invention has been described in terms of particular embodiments and applications, one of ordinary skill in the art, in light of this teaching, can generate additional embodiments and modifications without departing from the spirit of or exceeding the scope of the claimed invention. For example, the insertion and tretrieval of vials 28 may be accomplished in some cases by a telescoping retrieval and insertion mechanism which reaches into chamber 22. In that case, a lifting mechanism may be superfluous.

In addition, equivalent coolant circulation circuits include the pumping of coolant axially through chamber 22 rather than peripherally. In that case, distribution ring 144 may be smaller than that shown in FIG. 1.

Accordingly, it is to be understood that the drawings and descriptions herein are proferred by way of example to facilitate comprehension of the invention and should not be construed to limit the scope thereof.

What is claimed is:

1. A storage unit comprising:
   a housing defining a storage chamber;
   carrier means inside said chamber for carrying a plurality of specimens in a predetermined horizontal array;
   support means inside said chamber for carrying a second plurality of specimens in another horizontal array parallel to and vertically spaced from said predetermined horizontal array;
   drive means operatively connected to said carrier means and said support means for rotating said carrier means and said support means about a vertical axis;
   access means on said housing for enabling access to said chamber from above said carrier means; and
   insertion and removal means at least partially mounted to said housing for alternately inserting and removing specimens from carrier means and said support means via said access means.

2. The storage unit defined in claim 1 wherein said insertion and removal means includes an arm mounted outside said storage chamber.

3. The storage unit defined in claim 2 wherein said insertion and removal means further includes lifting means disposed at least partially inside said storage chamber for moving specimens vertically between said arm and said carrier means and between said arm and said support means.

4. The storage unit defined in claim 3 wherein said lifting means includes a lifting arm and means disposed vertically along an inner surface of said storage chamber for vertically reciprocating said lifting arm.

5. The storage unit defined in claim 3 wherein said lifting means includes a lifting arm and means disposed axially in said storage chamber for vertically reciprocating said lifting arm.

6. The storage unit defined in claim 1 wherein said insertion and removal means includes interchangeable adaptor means for varying the number of specimens which can be inserted and removed from said storage chamber by said insertion and removal means.

7. The storage unit defined in claim 1 wherein said drive means includes means for alternately rotating said carrier means and said support means about said vertical axis.

8. The storage unit defined in claim 1 wherein said drive means includes a drive member disposed axially with respect to said carrier means and said storage chamber.

9. The storage unit defined in claim 1, further comprising cooling means for maintaining said chamber in a predetermined low temperature range.

10. The storage unit defined in claim 9 wherein said cooling means includes circulating means for circulating a fluid coolant from a bottom portion of said chamber to an upper portion of said chamber above said carrier means.

11. The storage unit defined in claim 10 wherein said circulating means includes means for drawing said fluid coolant from a sump in said bottom portion.

12. The storage unit defined in claim 11, further comprising sensor means communicating with said sump for detecting ice build-up in said sump.

13. The storage unit defined in claim 10 wherein said carrier means and said support means are relatively disposed so that coolant runoff from said carrier means falls to said support means.

14. The storage unit defined in claim 1, further comprising verification means including but not limited to, an infrared sensor, a tactile detector, a holographic device or an acoustic sensor, for confirming the identities of specimens being retrieved from said storage chamber.

15. The storage unit defined in claim 1, further comprising cooling means for maintaining said storage chamber within a predetermined low temperature range, also comprising means for defining a buffer chamber communicating with said storage chamber via said access means during operation of said insertion and removal means, whereby exposure of specimens to ambient temperatures is minimized.

16. The storage unit defined in claim 1, further comprising additional access means for enabling access to said chamber laterally to said carrier means.

17. The storage unit defined in claim 1 wherein each of said carrier means and said support means includes a shelf and a plurality of trays removably disposed on said shelf.

18. The storage unit defined in claim 1 wherein at least some of said specimens are contained in receptacles on said carrier means.

19. A storage unit comprising:
   a housing defining a storage chamber;
   first carrier means inside said chamber for carrying a plurality of specimens in a first predetermined array in a first horizontal plane;
   second carrier means inside said chamber for carrying a plurality of specimens in a second predetermined array in a second horizontal plane spaced from and generally parallel to said first horizontal plane; and
   drive means operatively connected to said first carrier means and said second carrier means for automatically rotating said first carrier means and said second carrier means independently of one another about a vertical axis.

20. The storage unit defined in claim 19 wherein said first horizontal plane is disposed above said second horizontal plane, further comprising:
   access means on said housing for enabling access to said chamber from above said first horizontal plane; and
   insertion and removal means for alternately inserting and removing specimens from said first carrier means and said second carrier means via said access means,
   said first carrier means being provided with an aperture enabling insertion and removal of specimens from said second carrier means.

21. The storage unit defined in claim 20 wherein said insertion and removal means includes an arm mounted outside said storage chamber.

22. The storage unit defined in claim 21 wherein said insertion and removal means further includes lifting means disposed at least partially inside said storage chamber for moving specimens vertically between said arm and said carrier means.

23. The storage unit defined in claim 22 wherein said lifting means includes a lifting arm and means disposed vertically along an inner surface of said storage chamber for vertically reciprocating said lifting arm.

24. The storage unit defined in claim 22 wherein said lifting means includes a lifting arm and means disposed vertically along an axis of said storage chamber for vertically reciprocating said lifting arm.

25. The storage unit defined in claim 20 wherein said insertion and removal means includes interchangeable adaptor means for varying the number of specimens which can be inserted and removed from said storage chamber by said insertion and removal means.

26. The storage unit defined in claim 20, further comprising verification means including but not limited to, an infrared sensor, a tactile detector, a holographic device or an acoustic sensor, for confirming the identities of specimens being retrieved from said storage chamber.

27. The storage unit defined in claim 19, further comprising cooling means for maintaining said chamber in a predetermined low temperature range.

28. The storage unit defined in claim 27 wherein said cooling means includes circulating means for circulating a fluid coolant from a bottom portion of said chamber to an upper portion of said chamber above said carrier means.

29. The storage unit defined in claim 28 wherein said circulating means includes means for drawing said fluid coolant from a sump in said bottom portion.

30. The storage unit defined in claim 29, further comprising sensor means communicating with said sump for detecting ice build-up in said sump.

31. The storage unit defined in claim 28 wherein said first carrier means and said second carrier means are relatively disposed so that coolant runoff from said first carrier means falls to said second carrier means.

32. The storage unit defined in claim 19, further comprising cooling means for maintaining said storage chamber within a predetermined low temperature range, also comprising means for defining a buffer chamber communicating with said storage chamber via said access means during operation of said insertion and removal means, whereby exposure of specimens to ambient temperatures is minimized.

33. The storage unit defined in claim 19 wherein said drive means includes a drive member disposed axially with respect to said carrier means and said storage chamber.

34. The storage unit defined in claim 19, further comprising additional access means for enabling access to said chamber laterally to said carrier means.

35. The storage unit defined in claim 19 wherein at least one of said first said carrier means and said second carrier means includes a shelf and a plurality of trays removably disposed on said shelf.

36. The storage unit defined in claim 19 wherein at least some of said specimens are contained in receptacles on said carrier means.

37. A low-temperature storage unit comprising:
a housing defining a storage chamber;
carrier means inside said chamber for carrying a plurality of specimens in a predetermined horizontal array;
support means inside said chamber for carrying a second plurality of specimens in another horizontal array parallel to said predetermined horizontal array;
drive means operatively connected to said carrier means and said support means for rotating said carrier means and said support means about a vertical axis;
insertion and removal means at least partially mounted to said housing for alternately inserting and removing specimens from said carrier means and said support means; and
cooling means connected to said housing for maintaining said chamber in a predetermined sub-freezing temperature range.

38. The storage unit defined in claim 37 wherein said cooling means includes circulating means for circulating a fluid coolant from a bottom portion of said chamber to an upper portion of said chamber above said carrier means.

39. The storage unit defined in claim 38 wherein said circulating means includes means for drawing said fluid coolant from a sump in said bottom portion.

40. The storage unit defined in claim 39, further comprising sensor means communicating with said sump for detecting ice build-up in said sump.

41. The storage unit defined in claim 37 wherein said drive means includes means for alternately rotating said carrier means and said support means about said vertical axis.

42. The storage unit defined in claim 37 wherein said carrier means and said support means are relatively disposed so that coolant runoff from said carrier means falls to said support means.

43. The storage unit defined in claim 37, further comprising verification means including but not limited to, an infrared sensor, a tactile detector, a holographic device or an acoustic sensor, for confirming the identities of specimens being retrieved from said storage chamber.

44. The storage unit defined in claim 37, further comprising access means for enabling access to said chamber laterally to said carrier means.

45. The storage unit defined in claim 37 wherein each of said carrier means and said support means includes a shelf and a plurality of trays removably disposed on said shelf.

46. The storage unit defined in claim 37 wherein at least some of said specimens are contained in receptacles on said carrier means.

47. A low-temperature storage unit comprising:
a housing defining a storage chamber;
first support means inside said chamber for supporting a plurality of specimens in a first horizontal plane;
second support means inside said chamber for supporting a plurality of specimens in a second horizontal plane spaced from and generally parallel to said first horizontal plane;
insertion and removal means at least partially mounted to said housing for alternately inserting and removing specimens from said first support means and said second support means; and circulating means operatively connected to said housing for circulating a fluid coolant from a sump in a bottom portion of said chamber to said first support means, said first support means and said second support means being relatively disposed so that coolant runoff from said first support means falls to said second support means.

48. The storage unit defined in claim 47, further comprising drive means for alternately rotating said first support means and said second support means respectively in said first horizontal plane and said second horizontal plane about a common vertical axis.

49. A low-temperature storage unit comprising:
a housing defining a storage chamber;
a plurality of carrier trays inside said chamber;
means in said housing for rotatably supporting said carrier trays one above the other;
a plurality of specimens on each of said carrier trays;
drive means at least partially mounted to said housing and operatively connected to said carrier trays for automatically rotating said carrier trays independently of one another about a vertical axis;
circulating means attached to said housing for circulating a fluid coolant from a sump in a bottom portion of said chamber to one of said carrier trays;
means in said housing for guiding run-off coolant from said one of said carrier trays to another of said carrier trays disposed below said one of said carrier trays;
access means on said housing for enabling access to said chamber from above all of said carrier trays;
insertion and removal means at least partially mounted to said housing for alternately inserting and removing specimens from said chamber via said access means, a plurality of said carrier trays being provided with alignable apertures for enabling access to specimens in lower ones of said carrier trays through upper ones of said trays; and
control means operatively connected to said insertion and removal means for automatically tracking the locations of specimens in said housing and for controlling the insertion and removal of specimens from said chamber.

50. A low-temperature storage unit comprising:
a housing defining a plurality of separate storage chambers;
first cooling means in said housing for circulating a first coolant to maintain a first one of said chambers at a first predetermined low temperature;
second cooling means in said housing for circulating a second coolant to maintain a second one of said chambers at a second predetermined low temperature different from said first temperature;
first carrier means inside said first one of said chambers for carrying a first plurality of specimens in a first predetermined horizontal array;
second carrier means inside said second one of said chambers for carrying a second plurality of specimens in a second predetermined horizontal array;
drive means operatively connected to said first carrier means and said second carrier means for rotating said first carrier means and said second carrier means independently about a vertical axis;
insertion and removal means at least partially mounted to said housing for alternately inserting and removing specimens from said first carrier means and said second carrier means.

51. The storage unit defined in claim 50, further comprising thawing and freezing enclosures accessible by said insertion and retrieval means.

* * * * *